(12) United States Patent
Bryan

(10) Patent No.: US 9,809,464 B2
(45) Date of Patent: Nov. 7, 2017

(54) APPARATUS FOR HARVESTING ALGAE FROM OPEN BODY OF WATER

(71) Applicant: Kent A. Bryan, Celina, OH (US)

(72) Inventor: Kent A. Bryan, Celina, OH (US)

( * ) Notice: Subject to any disclaimer, the term of this patent is extended or adjusted under 35 U.S.C. 154(b) by 398 days.

(21) Appl. No.: 14/540,309

(22) Filed: Nov. 13, 2014

(65) Prior Publication Data

US 2015/0128838 A1 May 14, 2015

Related U.S. Application Data

(60) Provisional application No. 61/903,481, filed on Nov. 13, 2013.

(51) Int. Cl.
*C02F 1/24* (2006.01)
*E02B 15/04* (2006.01)
(Continued)

(52) U.S. Cl.
CPC ............... *C02F 1/24* (2013.01); *A01D 44/00* (2013.01); *A01G 33/00* (2013.01); *B03D 1/1431* (2013.01);
(Continued)

(58) Field of Classification Search
CPC ....... E02B 15/04; E02B 15/046; A01D 44/00; A01G 33/00; B03D 1/1431; B03D 2203/001; C02F 1/24; C02F 2103/007; B63B 35/32; C12M 1/09
USPC ... 210/747.6, 170.05, 170.06, 170.09, 170.1, 210/170.11, 242.1, 242.2, 703, 221.2; 56/8; 47/1.4
See application file for complete search history.

(56) References Cited

U.S. PATENT DOCUMENTS 4,176,058 A * 11/1979 Grobler .................... C02F 1/24
210/747.5
4,690,756 A * 9/1987 Van Ry .................... C02F 1/24
210/170.06
(Continued)

FOREIGN PATENT DOCUMENTS

CN 1143826 C 3/2004
CN 201071106 Y 6/2008
(Continued)

OTHER PUBLICATIONS

The Daily Standard, William Kincaid, "Official floats idea to build boat that harvest algae," Apr. 1, 2011, Retrieved from Web on Oct. 2, 2013: <http://www.dailystandard.com/archive/2011-04-01/stories/14565/official-floats-idea-to-build-boat-that-harvests-algae>.

*Primary Examiner* — Christopher Upton
(74) *Attorney, Agent, or Firm* — William J. Clemens; Shumaker, Loop & Kendrick, LLP

(57) ABSTRACT

An apparatus for harvesting algae from an open body of water includes a boat having a pair of spaced apart parallel flotation members and a deck disposed on and connected to the members. The spaced apart members define an area therebetween forming a process channel. A separating mechanism disposed on the boat separates the process channel into a plurality of process channel sections arranged in series. The process channel sections are disposed intermediate the flotation members. Each of the process channel sections include a deflector plate, a scum beach, a scum trough, and diffused air piping. The diffused air piping is in fluid communication with a dissolved air flotation system.

17 Claims, 13 Drawing Sheets

(51) Int. Cl.

| | | |
|---|---|---|
| *A01D 44/00* | (2006.01) | |
| *C12M 1/00* | (2006.01) | |
| *C12M 1/09* | (2006.01) | |
| *C12M 1/26* | (2006.01) | |
| *A01G 33/00* | (2006.01) | |
| *C10L 5/44* | (2006.01) | |
| *B03D 1/14* | (2006.01) | |
| *B63B 35/32* | (2006.01) | |
| *C02F 103/00* | (2006.01) | |
| *B63B 35/34* | (2006.01) | |

(52) U.S. Cl.
CPC .............. *B63B 35/32* (2013.01); *C10L 5/445* (2013.01); *C12M 21/02* (2013.01); *C12M 23/18* (2013.01); *C12M 23/56* (2013.01); *C12M 33/00* (2013.01); *C12M 47/02* (2013.01); *E02B 15/04* (2013.01); *B03D 2203/001* (2013.01); *B63B 35/34* (2013.01); *C02F 2103/007* (2013.01); *C02F 2201/008* (2013.01); *C02F 2301/066* (2013.01); *Y02E 50/10* (2013.01); *Y02E 50/30* (2013.01)

(56) References Cited

U.S. PATENT DOCUMENTS

| | | | | |
|---|---|---|---|---|
| 5,223,130 | A * | 6/1993 | Valfrido | .................... C02F 1/24 |
| | | | | 210/170.05 |
| 7,101,478 | B2 * | 9/2006 | Corradi | .................. B01D 19/02 |
| | | | | 210/170.09 |
| 7,255,332 | B2 * | 8/2007 | Osborn | ..................... C02F 7/00 |
| | | | | 210/221.2 |
| 7,452,462 | B2 * | 11/2008 | Joliet | ...................... B63B 35/32 |
| | | | | 210/170.05 |
| 2002/0079270 | A1 * | 6/2002 | Borodyanski | ............. C02F 1/24 |
| | | | | 210/221.2 |
| 2012/0168385 | A1 | 7/2012 | Anderson | |
| 2012/0228232 | A1 | 9/2012 | Jensen et al. | |

FOREIGN PATENT DOCUMENTS

| | | |
|---|---|---|
| CN | 101671060 A | 3/2010 |
| CN | 101691249 B | 6/2011 |
| CN | 103288160 A | 9/2013 |
| CN | 103318983 A | 9/2013 |
| JP | S6073910 A | 4/1985 |
| JP | 2007160178 A | 6/2007 |
| JP | 2008063823 A | 3/2008 |

* cited by examiner

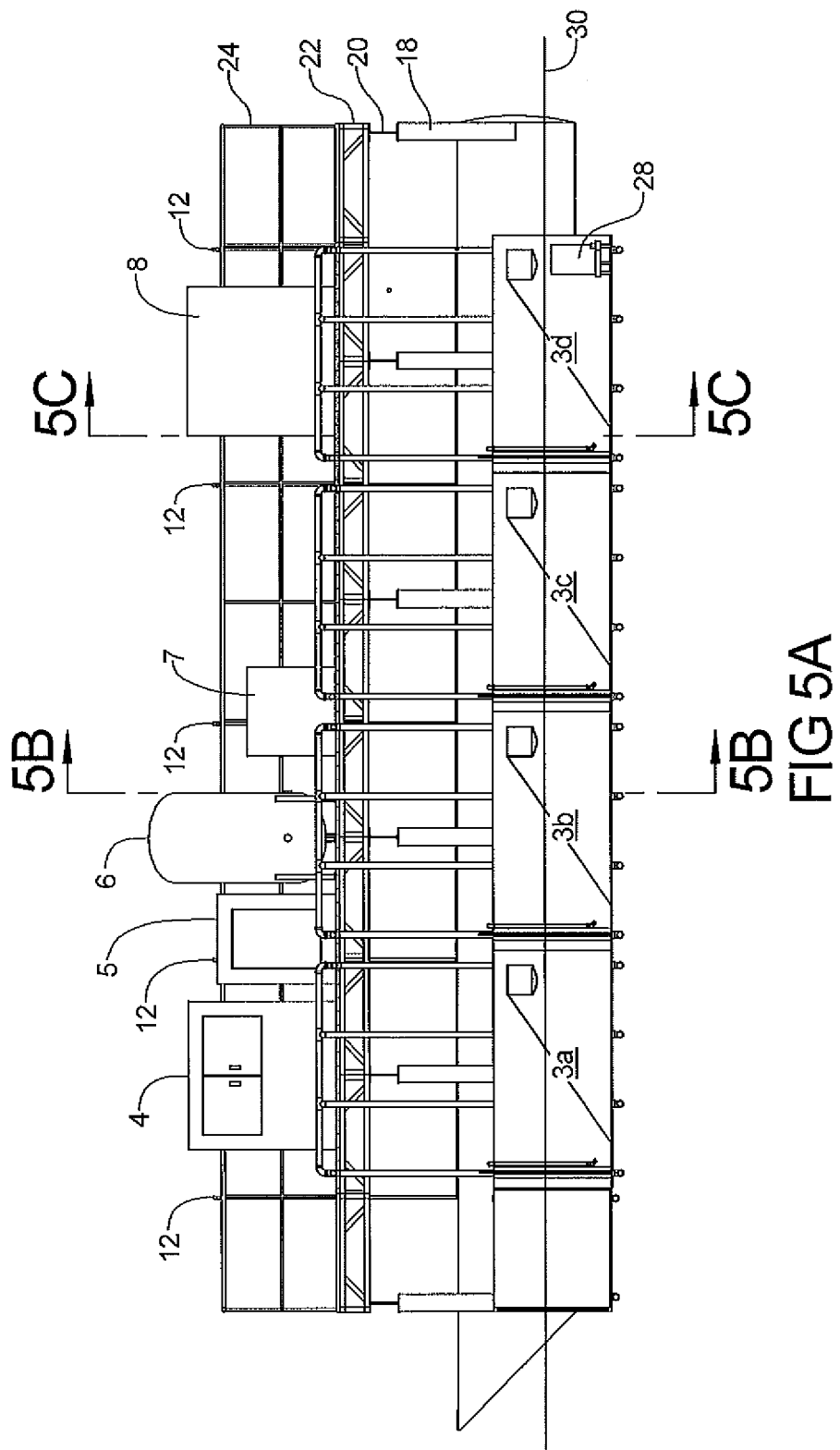

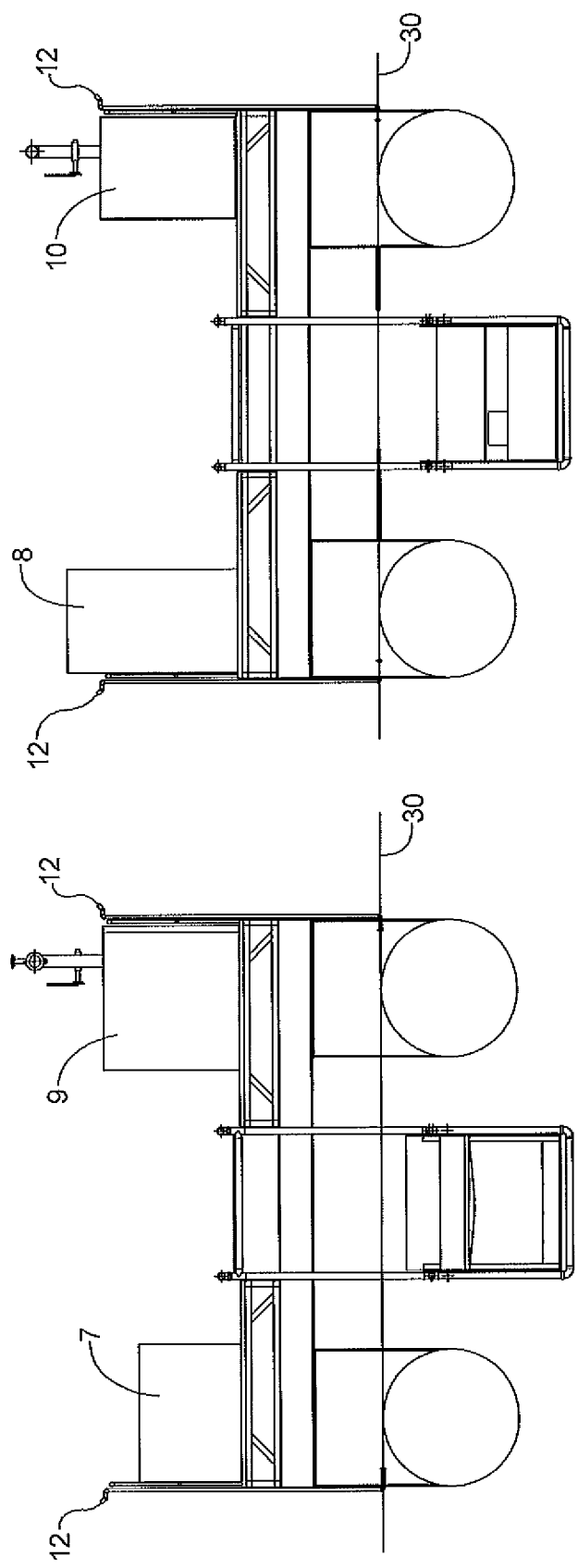

APPARATUS FOR HARVESTING ALGAE FROM OPEN BODY OF WATER

CROSS REFERENCE TO RELATED APPLICATIONS

This application claims the benefit of U.S. Provisional Application No. 61/903,481, filed on Nov. 13, 2013. The entire disclosure of the above application is incorporated herein by reference.

FIELD

This invention relates to water treatment by dissolved air floatation and, more particularly, harvesting algae from an open body of water utilizing dissolved air floatation technology.

BACKGROUND

This section provides background information related to the present disclosure which is not necessarily prior art.

Dissolved air flotation (DAF) is a water treatment process that clarifies wastewaters (or other waters) by the removal of suspended matter such as oil or solids. The removal is achieved by dissolving air in the water or wastewater under pressure and then releasing the air at atmospheric pressure in a flotation tank or basin. The released air forms tiny bubbles which adhere to the suspended matter causing the suspended matter to float to the surface of the water where it may then be removed by a skimming device.

Dissolved air flotation is very widely used in treating the industrial wastewater effluents from oil refineries, petrochemical and chemical plants, natural gas processing plants, paper mills, general water treatment and similar industrial facilities. A very similar process known as induced gas flotation is also used for wastewater treatment. Froth flotation is commonly used in the processing of mineral ores.

The feed water to the DAF float tank is often (but not always) dosed with a coagulant (such as ferric chloride or aluminum sulfate) to flocculate the suspended matter.

A portion of the clarified effluent water leaving the DAF tank is pumped into a small pressure vessel (called the air drum) into which compressed air is also introduced. This results in saturating the pressurized effluent water with air. The air-saturated water stream is recycled to the front of the float tank and flows through a pressure reduction valve just as it enters the front of the float tank, which results in the air being released in the form of tiny bubbles. The bubbles adhere to the suspended matter, causing the suspended matter to float to the surface and form a froth layer which is then removed by a skimmer. The froth-free water exits the float tank as the clarified effluent from the DAF unit.

Some DAF unit designs utilize parallel plate packing material, lamellas, to provide more separation surface and therefore to enhance the separation efficiency of the unit.

DAF systems can be categorized as circular (more efficient) and rectangular (more residence time). The former type requires just 3 minutes; an example is a Wock-Oliver DAF system (www.wockoliver.com). The rectangular type requires 20 to 30 minutes; a typical example is a Syskill DAF system (www.syskill.com.au). One of the bigger advantages of the circular type is its spiral scoop. A typical DAF system is shown in the schematic diagram of FIG. 13.

The DAF Corporation (www.dafcorp.com) FC Maximizer clarifier is designed and manufactured for harvesting algae. It is a hybrid DAF clarifier. Algae feeds on carbon dioxide and sun light. Algae's biomass once refined can be used for animal feed or its lipid oil for blended petroleum based fuels. The FC Maximizer clarifier is a cost-effective way to harvest algae. It can also feed algae. Part of the FC Maximizer clarifier system is the AMT air dissolving system. It can be used to nourish algae with a side stream of $CO_2$ as a nutrient. This side stream of carbon dioxide with laden water and compressed air from this AMT is injected into the FC Maximizer clarifier as fine micron bubbles. These micron bubbles rise to the surface of the water in the tank at a rate 10" to 12" per minute. Hundreds of millions of all equal sized, fine micron bubbles entrap themselves in the suspended solids or algae bloom in the FC Maximizer tank.

Parallel with this process, on the open tank top rim is a rotating stainless steel tank carriage that supports the fixed and rotating tank internal parts. A stainless steel, variable speed, two blade rotating scoop is attached to it. Again, this design gently dips and scoops up the dense fine float mat and discharges it into a holding tank. Clean carbon dioxide enriched nutrient water is discharged from the clarifier tank. This water can be piped back into different systems for a multitude of uses.

The FC Maximizer clarifier is self-cleaning. It operates with minimal turbulence in a shallow round tank. The FC Maximizer clarifier will remove 98% of the algae bloom and lipid oil within the first two and a half minutes. The clarifier's wetted parts are all stainless steel. Sizes ranging from 20 gpm up to 9000 gpm are manufactured.

However, the prior art does not directly remove algae from open bodies of water on an in-lake basis utilizing dissolved air floatation technology.

SUMMARY

According to the present invention, the dissolved air floatation (DAF) equipment is mounted on a boat (catamaran or barge configuration) to remove microscopic algae directly from the water in lakes and ponds. One key element in the process is the utilization of DAF equipment. The lake water passes through a channel under the boat that allows for the processing of large volumes of water at low energy costs.

The boat would collect both algae and phosphorus by using the dissolved air flotation (DAF) technology. DAF uses tiny bubbles to cause algae to float to the surface of the water. The algae then would be skimmed and stored on the harvesting boat. By weight, 3 percent of algae is phosphorous. Therefore, if 100 pounds of algae were removed, three pounds of phosphorus also would be taken out of the body of water.

The collected algae would be conveyed to a storage facility for processing and/or transport. The algae can be used as a renewable biofuel in several forms. After processing of the algae for its biofuel value, the nutrient rich algal biomass can be used as a sellable, organic product.

An apparatus for harvesting algae from an open body of water includes a boat having a pair of spaced apart parallel flotation members and a deck disposed on and connected to the members. The spaced apart members define an area therebetween forming a process channel. A separating mechanism disposed on the boat separates the process channel into a plurality of process channel sections arranged in series. The process channel sections are disposed intermediate the flotation members. Each of the process channel sections include a deflector plate, a scum beach, a scum trough, and diffused air piping. The diffused air piping is in fluid communication with a dissolved air flotation system.

DRAWINGS

The above as well as other advantages of the present invention will become readily apparent to those skilled in the art from the following detailed description of a preferred embodiment when considered in the light of the accompanying drawings in which:

FIG. 5A is a side elevational view of the boat shown in FIG. 1;

FIGS. 5B, 5C are perspective views of the boat shown in FIG. 5;

DESCRIPTION

The following detailed description and appended drawings describe and illustrate various exemplary embodiments of the invention. The description and drawings serve to enable one skilled in the art to make and use the invention, and are not intended to limit the scope of the invention in any manner. In respect of the methods disclosed, the steps presented are exemplary in nature, and thus, the order of the steps is not necessary or critical.

Figure 1:
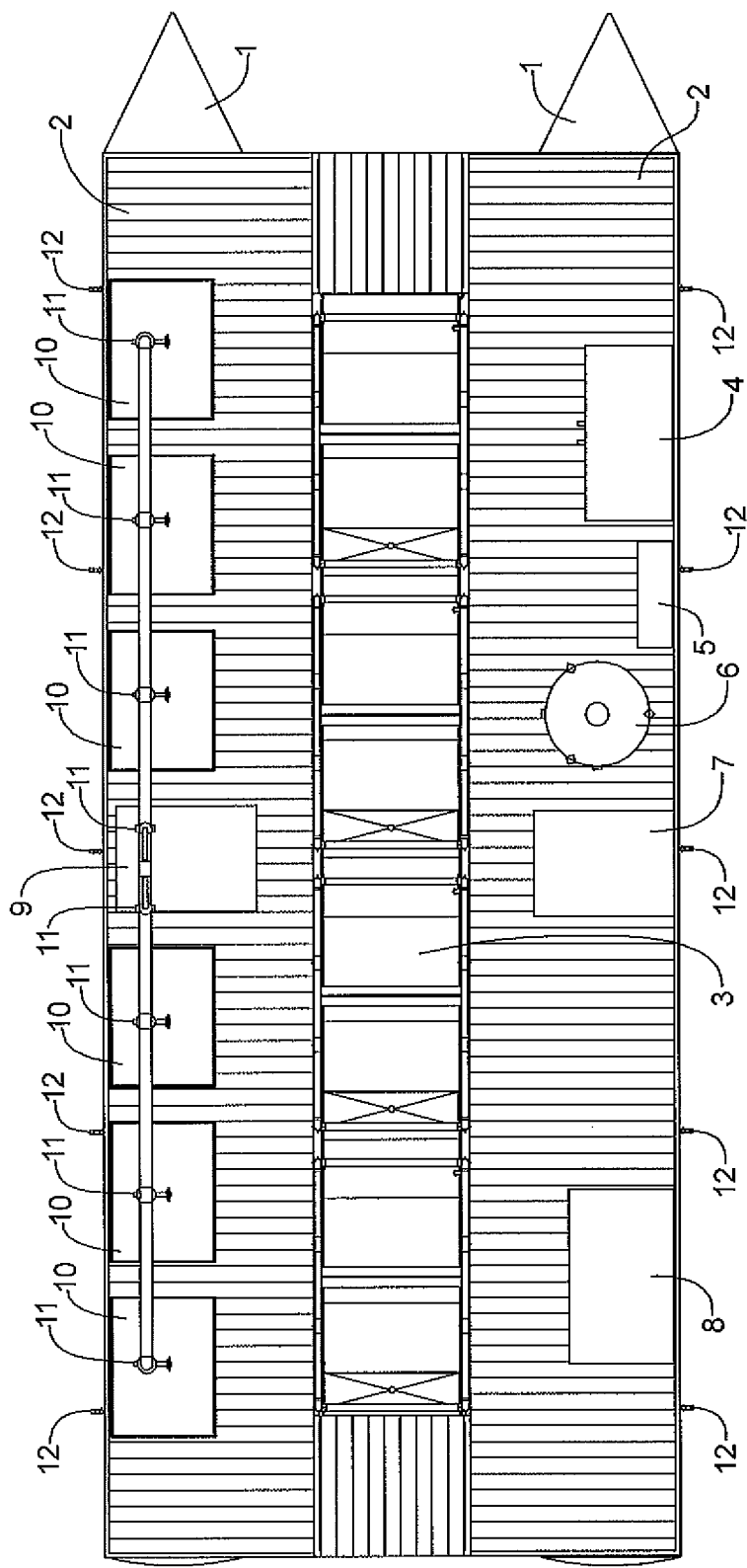
FIG. 1 is a top plan view of an algae harvesting boat according to the invention.

Referring to FIG. 1, an algae harvesting boat includes two aluminum members which according to several aspects define pontoons 1 (having exemplary dimensions of 48" diameter×40' long) thereby providing flotation members supporting a non-skid deck on an aluminum frame 2. A 48" wide process channel 3 having multiple individual channel sections is defined by and positioned between the pontoons 1. Mounted on the deck are a generator unit 4, an electrical distribution panel 5, a saturator 6, a DAF pump 7, a DAF air compressor 8, a vacuum pump 9, multiple algae storage tanks 10 individually receiving material from one of the multiple channel sections, 4" butterfly valves 11 and oxygenation spray nozzles 12.

Figure 2:
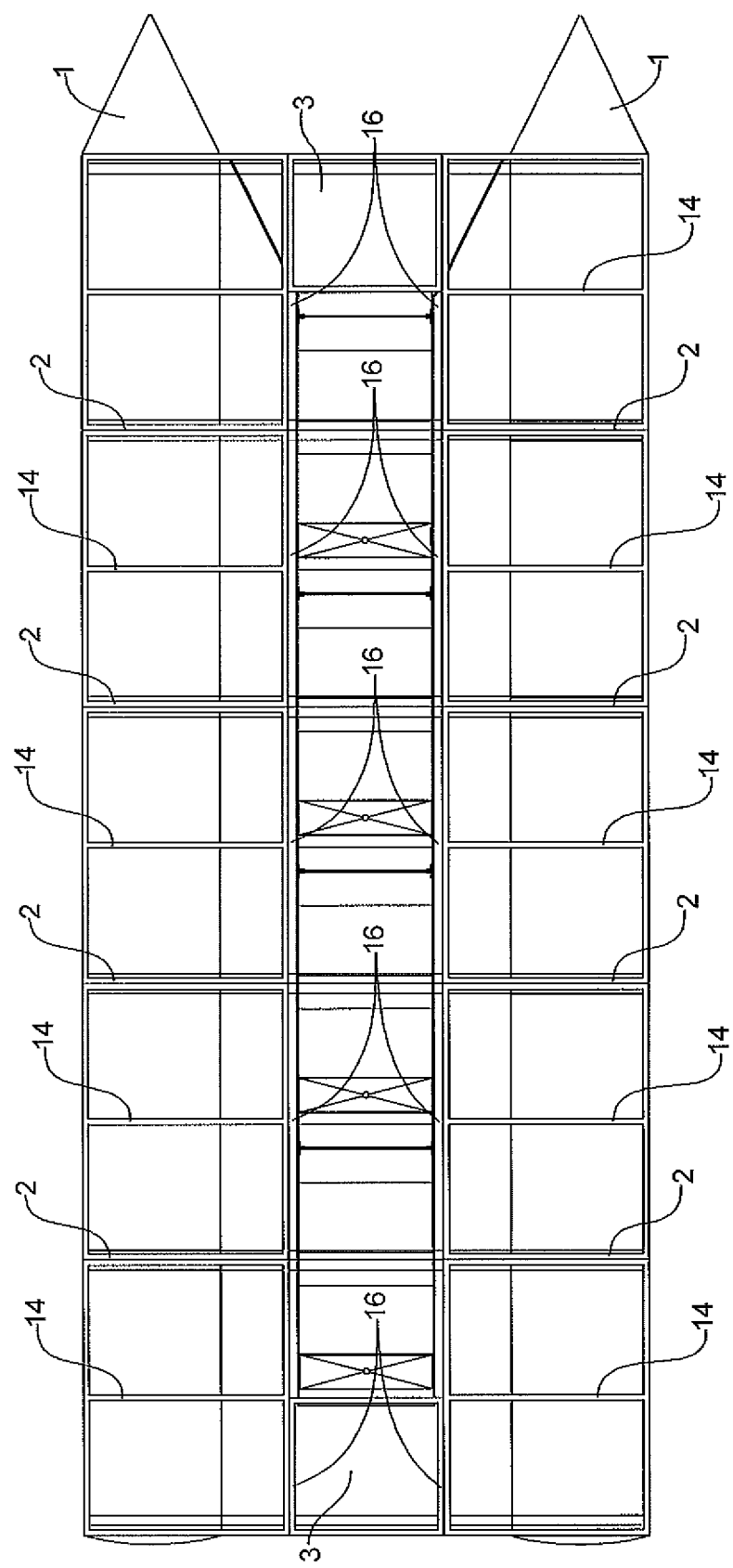
FIG. 2 is structural framing plan for the boat shown in FIG. 1.

Referring to FIG. 2, the structural framing for the boat includes the two aluminum pontoons 1, the aluminum structural beam framing 2, and the 48" wide process channel 3. Welded deck framing 14 and aluminum channel framing 16 are also provided.

Figure 3:
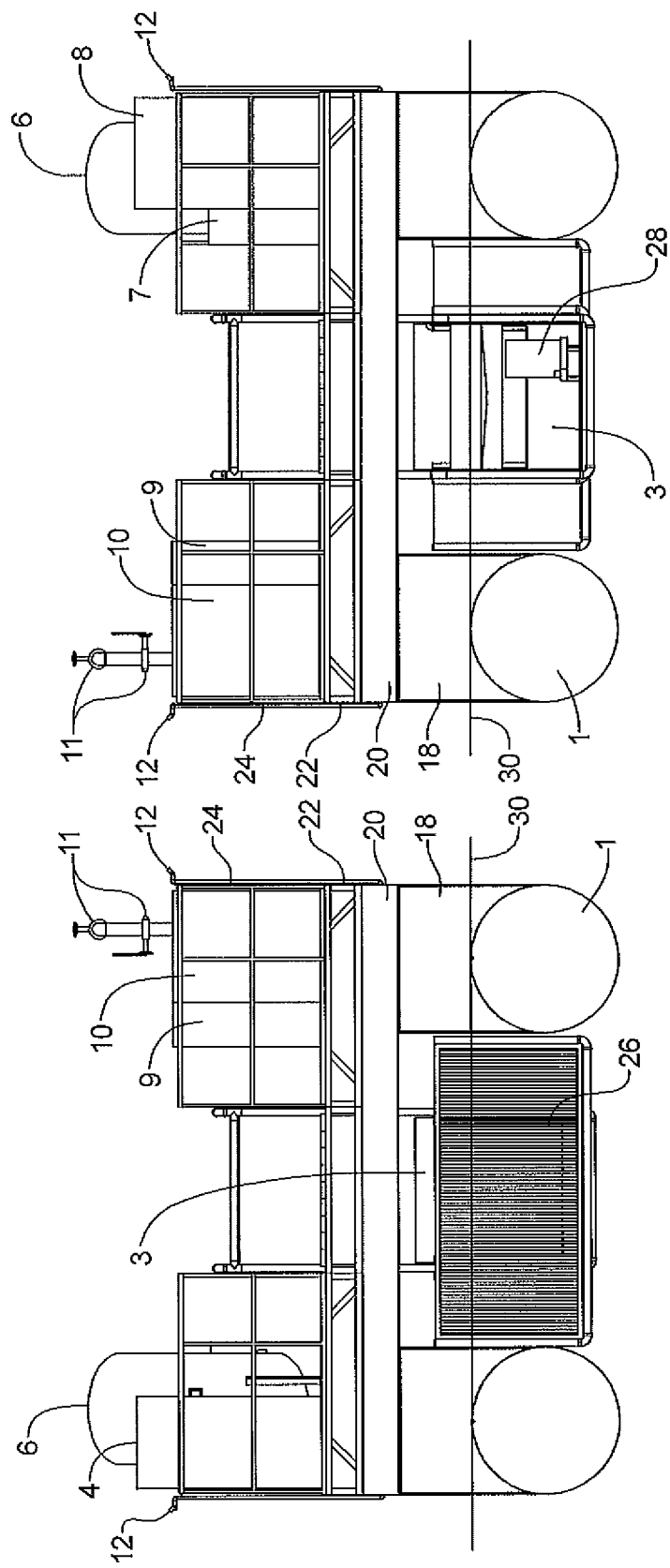
FIGS. 3A and 3B are front and rear views of the boat shown in FIG. 1.

Referring to FIGS. 3A and 3B, front and rear views respectively of the boat include the two aluminum pontoons 1, 24" welded riser sections 18, 12" aluminum beam framing 20, 12" deck with integral framing 22, a 42" safety handrail 24, a 48" tall by 96" wide trash guard 26 at an inlet of the process channel 3, the generator unit 4, the saturator 6, the DAF pump 7, the DAF air compressor 8, the vacuum pump 9, a submersible fountain pump 28, the 4" butterfly valves 11, the algae storage tank 10, the multiple oxygenation spray nozzles 12. The trash guard 26 is positioned at the forward end of the process channel 3 and at least partially below a water level 30 to permit entrance of the water containing the algae, but to block large elements from entering the process channel 3.

Figure 4:
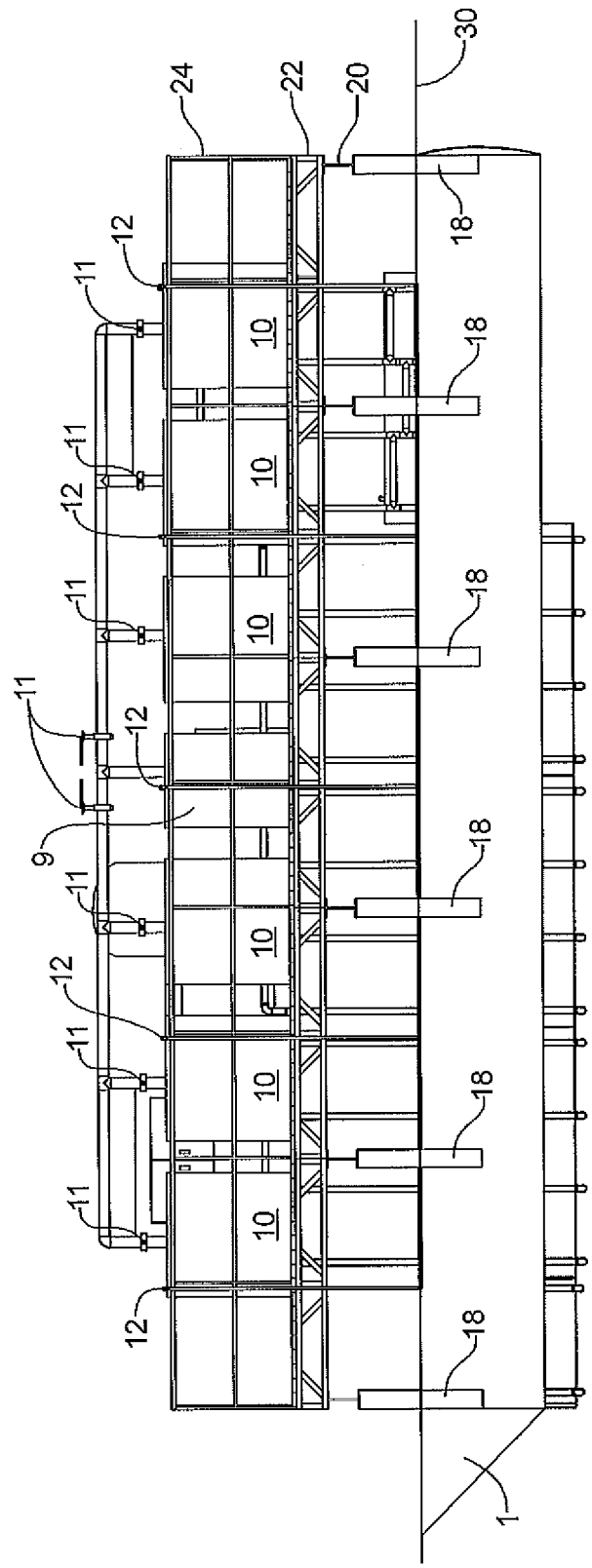
FIG. 4 is a side view of the boat shown in FIG. 1.

Referring to FIG. 4, the boat includes the aluminum pontoons 1, the 24" welded riser sections 18, the 12" aluminum beam framing 20, the 12" deck with integral framing 22, the 42" safety handrail 24, the vacuum pump 9, the multiple 4" butterfly valves 11, the algae storage tanks 10, and the oxygenation spray nozzles 12.

Referring to FIGS. 5A-5C, side elevational and sectional views of the boat include the two aluminum pontoons 1, the 24" welded riser sections 18, the 12" aluminum beam framing 20, the 12" deck with integral framing 22, the 42" safety handrail 24, the 48" wide by 96" long process channel sections 3a, 3b, 3c, 3d, the trash guard 26, the generator unit 4, the electrical distribution panel 5, the saturator 6, the DAF pump 7, the DAF air compressor 8, the submersible fountain pump 28, the oxygenation spray nozzles 12, the vacuum pump 9, the algae storage tanks 10, and the water level 30.

Figure 6:
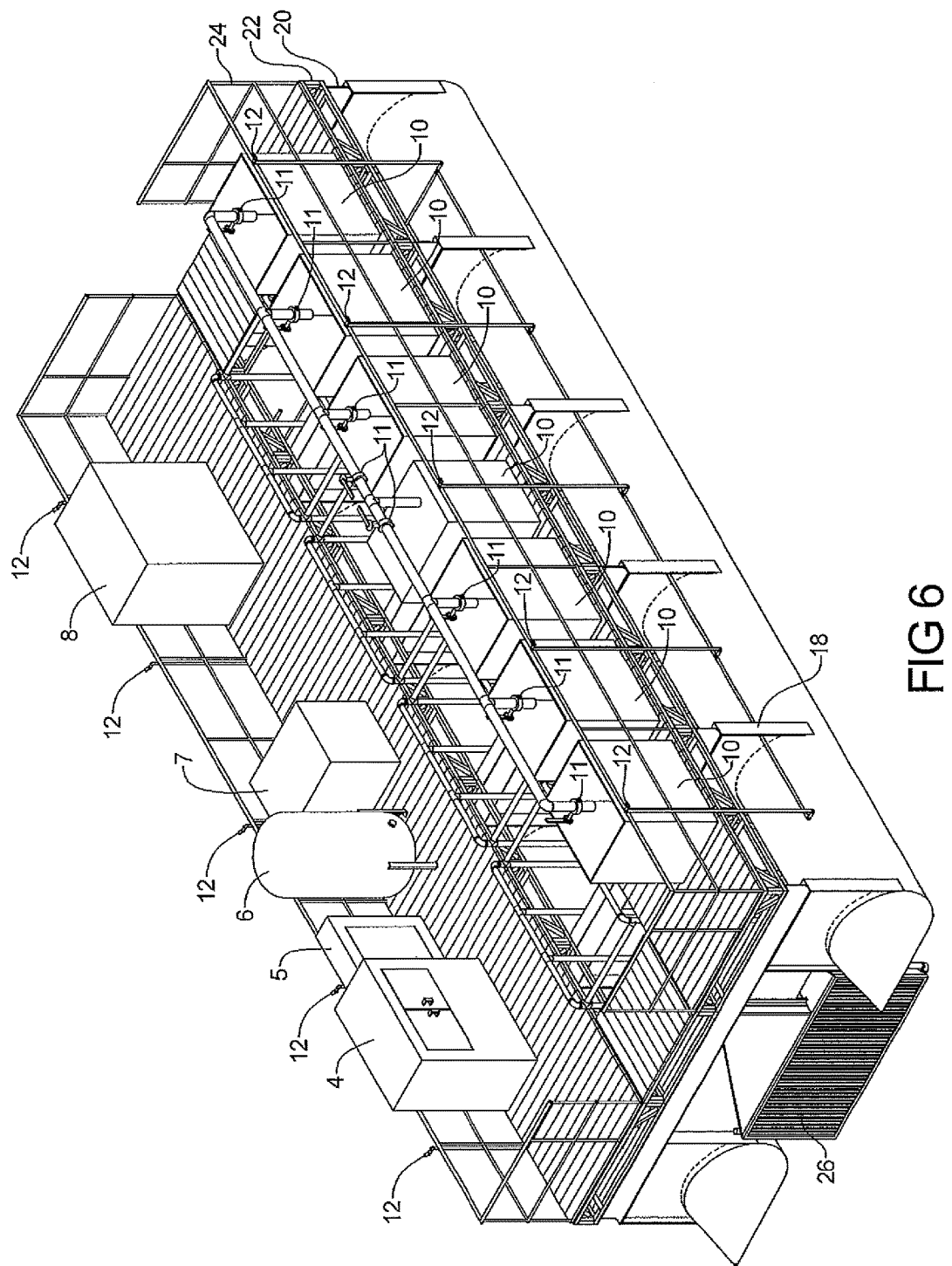
FIG. 6 is a front left perspective view of the boat shown in FIG. 1.

Referring to FIG. 6, in a perspective view of the boat shown are the two aluminum pontoons 1, the 24" welded riser sections 18, 12" the aluminum beam framing 20, the 12" deck with integral framing 22, the 42" safety handrail 24, the trash guard 26, the generator unit 4, the electrical distribution panel 5, the saturator 6, the DAF pump 7, the DAF air compressor 8, the 4" butterfly valves 11, the algae storage tanks 10, and oxygenation spray nozzles 12.

Figure 7:
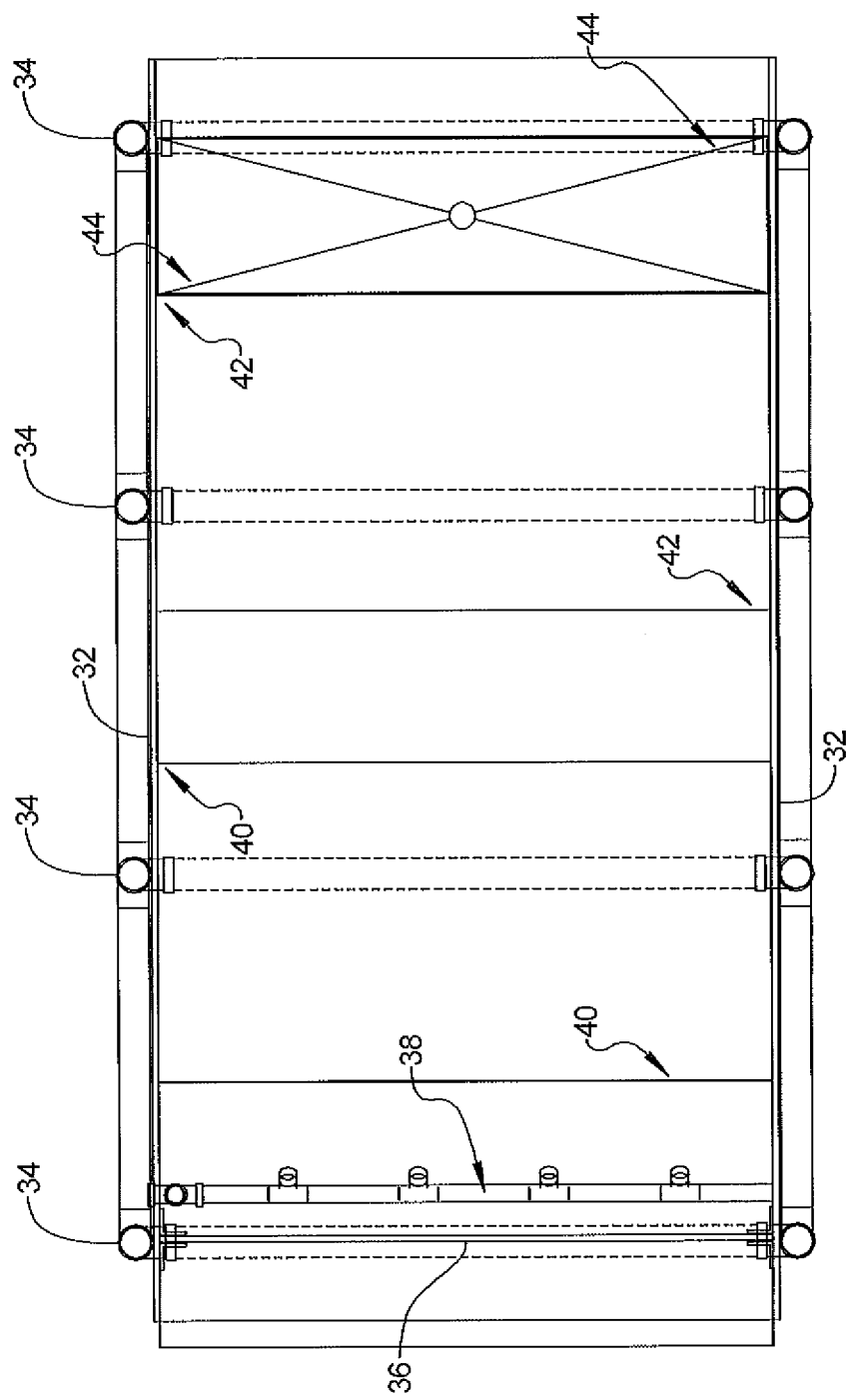
FIG. 7 is a top plan view of the process channel of the boat shown in FIG. 1.

Referring to FIG. 7, the process channel includes ½" thick (48"×96") solid vinyl sheeting 32, a plurality of 2" SCH80 piping supports 34, a 1" thick (48"×96") solid vinyl baffle 36, a gap 37 adjacent the solid vinyl baffle 36, multiple sections of 1" SCH80 diffused air piping 38, multiple ½" thick (24"×48") deflector plates 40, multiple ½" thick (24"×48") algae scum beaches 42, and a 12"×12"×48" solid vinyl scum trough 44.

Figure 8:
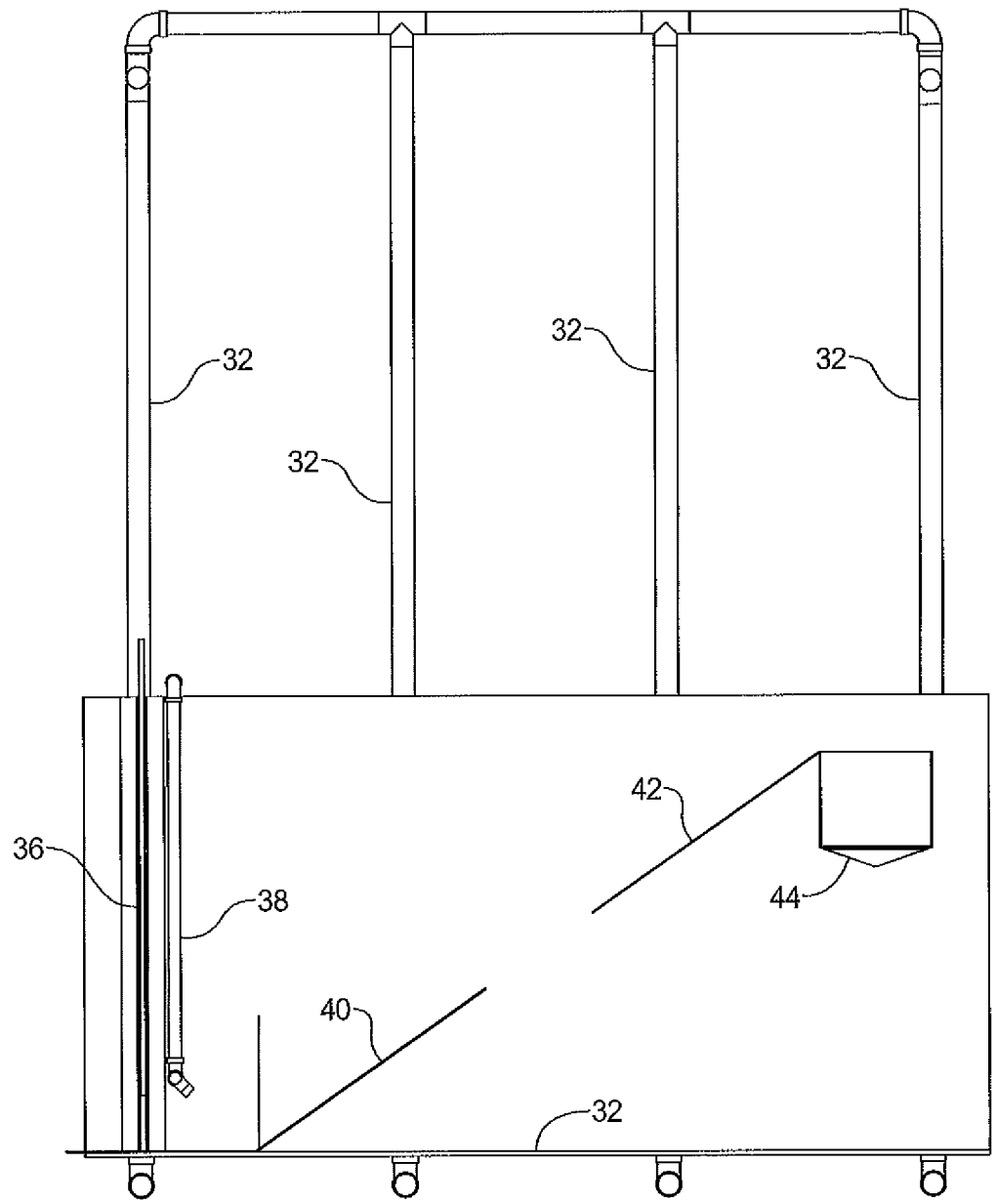
FIG. 8 is an end elevational view of the process channel shown in FIG. 7.

Referring to FIG. 8, the process channel 3 includes the solid vinyl sheeting 32, the piping supports 34, the solid vinyl baffle 36, the diffused air piping 38, the deflector plates 40, the algae scum beach 42, and the solid vinyl scum trough 44.

Figure 9:
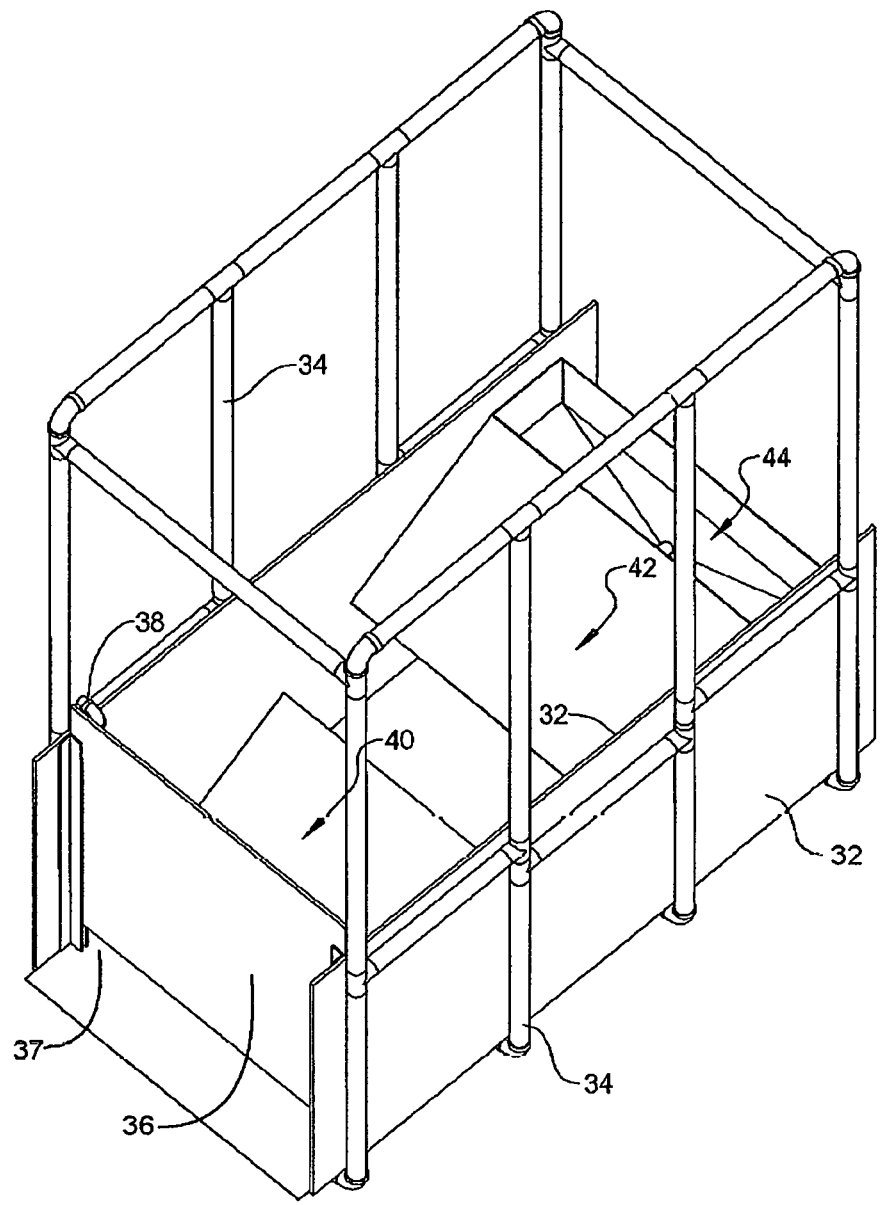
FIG. 9 is a front left perspective view of the process channel shown in FIG. 7.

Referring to FIG. 9, the process channel including the solid vinyl sheeting 32, the 2" SCH80 piping supports 34, the solid vinyl baffle 36, the diffused air piping 38, the deflector plates 40, the algae scum beach 42, and the solid vinyl scum trough 44.

Figure 10:
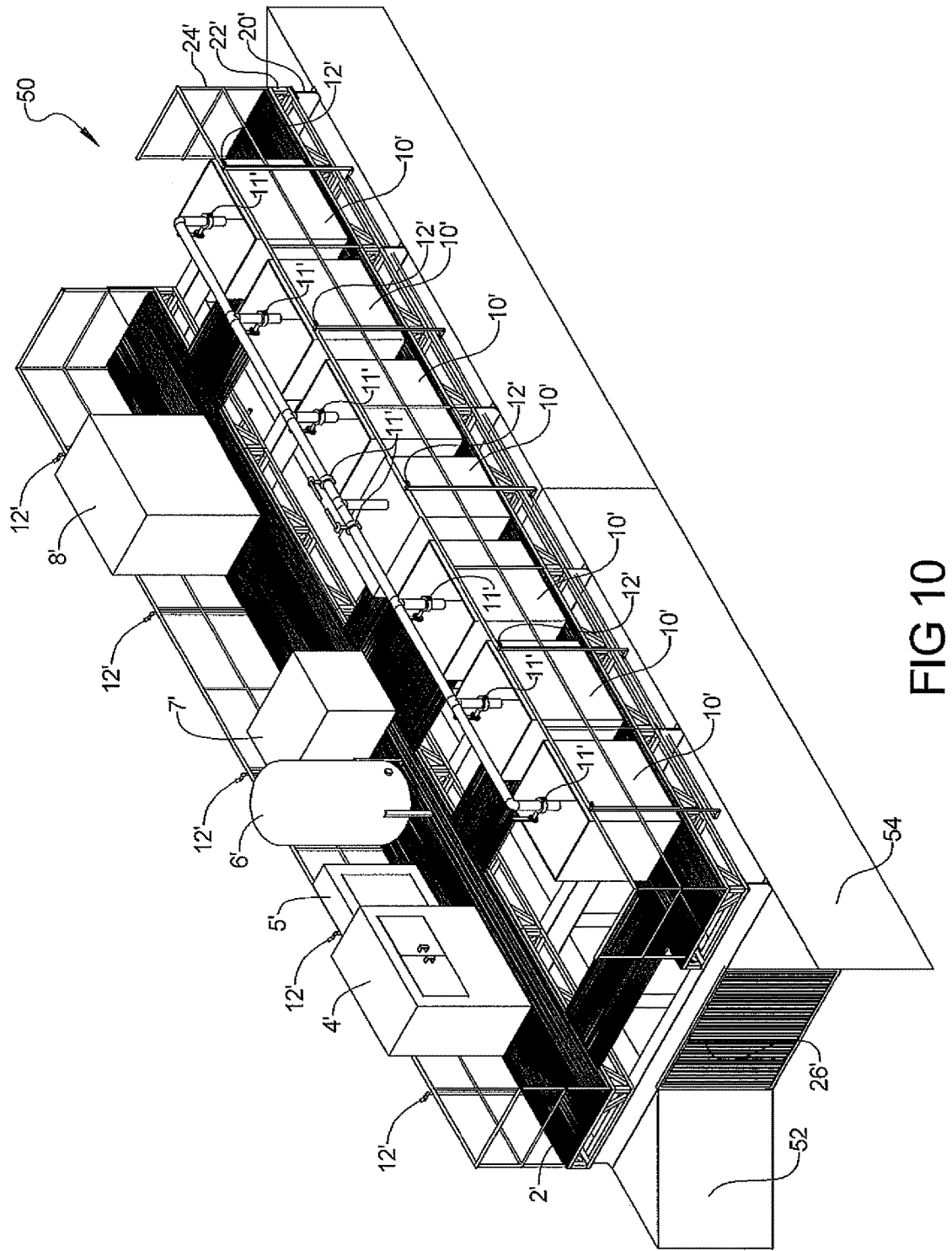
FIG. 10 is a front left perspective view of a boat of another aspect of the present disclosure.
Figure 11:
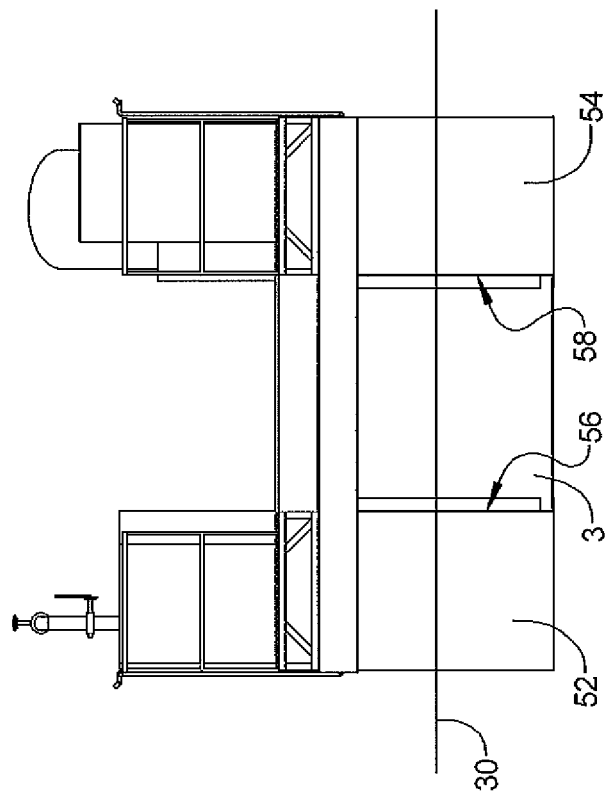
FIG. 11 is a front end elevational view of the boat of FIG. 10.
Figure 12:
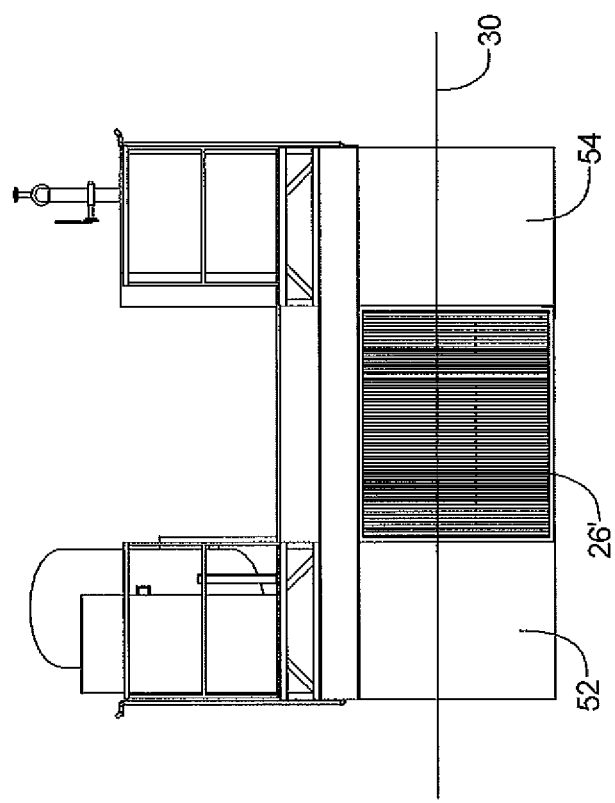
FIG. 12 is a rear end elevational view of the boat of FIG. 10.
Figure 13:
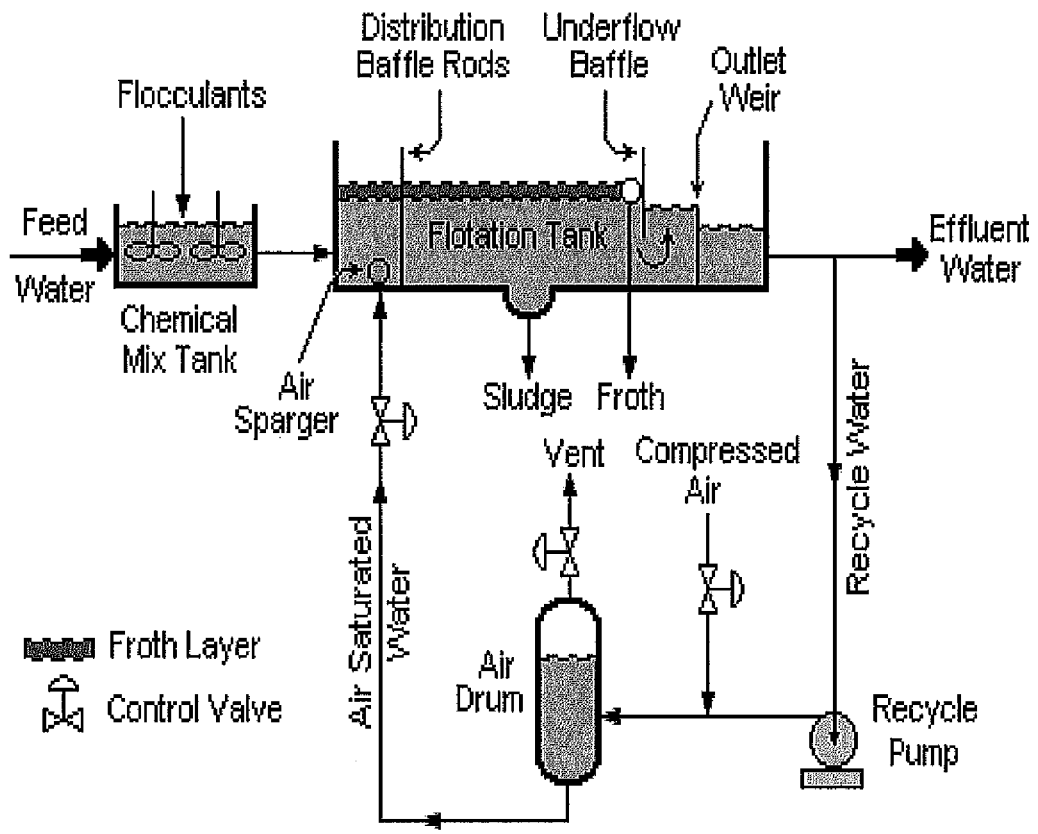
FIG. 13 is a diagram of a prior art dissolved air flotation system.

Referring to FIGS. 10-12, an algae harvesting boat 50 is modified from the algae harvesting boat of FIG. 1 to include two rectangular-shaped aluminum members which according to several aspects define pontoons 52, 54 (having exemplary dimensions of 48" wide×48" high ×40' long) which are used in place of the pontoons 1 of FIG. 1. The pontoons 52, 54 provide flat upper surfaces for attachment of the components of the system. Other components of algae harvesting boat 50 are substantially the same as the algae harvesting boat of FIG. 1. The pontoons 52, 54 provide flotation members supporting a non-skid deck on the aluminum frame 2'. The 48" wide process channel 3' having multiple individual channel sections is defined by and is positioned between the pontoons 52, 54. Mounted on the deck are the generator unit 4', the electrical distribution panel 5', the saturator 6', the DAF pump 7', the DAF air compressor 8', the vacuum pump 9', multiple algae storage tanks 10' individually receiving material from one of the multiple channel sections, the multiple 4" butterfly valves 11' and the multiple oxygenation spray nozzles 12'. The trash guard 26' is similarly located at the forward end of the process channel 3'.

With specific reference to FIG. 12 the rectangular-shaped pontoons 53, 54 provide opposed, planar surfaces 56, 58 which are substantially parallel to each other. The surfaces 56, 58 define the inner flow and boundary surfaces of the process channel 3' such that additional framing and components are not required to establish the boundary surfaces of the process channel 3' which may be required with the round pontoons 1 of the embodiment of FIG. 1. The flat upward facing surfaces of the pontoons 52, 54 also provide for direct connection of the support structure of the aluminum frame 2'.

In accordance with the provisions of the patent statutes, the present invention has been described in what is considered to represent its preferred embodiment. However, it should be noted that the invention can be practiced otherwise than as specifically illustrated and described without departing from its spirit or scope.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. An apparatus for harvesting algae from an open body of water, comprising:
    a boat having a pair of spaced apart parallel flotation members and a deck disposed on and connected to the members, the spaced apart members defining an area therebetween forming a process channel; and
    a separating mechanism disposed on the boat separating the process channel into a plurality of process channel sections arranged in series, the process channel sections disposed intermediate the flotation members, each of the process channel sections including at least one deflector plate below a water level, an algae scum beach crossing the water level, a scum trough coupled to the algae scum beach, and a diffused air piping, with the diffused air piping in fluid communication with a dissolved air flotation system.

2. The apparatus for harvesting algae from an open body of water of claim 1, further including a generator unit and an electrical distribution panel mounted on the deck, the generator unit operating to energize a saturator, a dissolved air flotation (DAF) pump, a DAF air compressor, and a vacuum pump.

3. The apparatus for harvesting algae from an open body of water of claim 1, further including a plurality of algae storage tanks mounted on the deck each collecting algae from one of the process channel sections.

4. The apparatus for harvesting algae from an open body of water of claim 1, wherein the spaced apart members comprise substantially flat walls, the walls acting to contain and direct algae received between the walls for feeding to the separating mechanism.

5. The apparatus for harvesting algae from an open body of water of claim 1, wherein the process channel includes vinyl sheeting defining walls of the process channel, a plurality of piping supports, a baffle, and multiple sections of the diffused air piping.

6. The apparatus for harvesting algae from an open body of water of claim 1, further including a trash guard at an inlet of the process channel.

7. The apparatus for harvesting algae from an open body of water of claim 1, further including a saturator, a dissolved air flotation (DAF) pump, a DAF air compressor, a vacuum pump, and multiple algae storage tanks each mounted on the deck.

8. An apparatus for harvesting algae from an open body of water, comprising:
   a boat having a pair of spaced apart parallel flotation members and a deck disposed on and connected to the members, the spaced apart members defining an area therebetween forming a process channel; and
   a separating mechanism disposed on the boat separating the process channel into a plurality of process channel sections arranged in series, the process channel sections disposed intermediate the flotation members, each of the process channel sections including a deflector plate below a water level, a scum beach crossing the water level, a scum trough coupled to the scum beach, and diffused air piping, with the diffused air piping in fluid communication with a dissolved air flotation system.

9. The apparatus for harvesting algae from an open body of water of claim 8, further including a generator unit and an electrical distribution panel mounted on the deck, the generator unit operating to energize a saturator, a dissolved air flotation (DAF) pump, a DAF air compressor, and a vacuum pump.

10. The apparatus for harvesting algae from an open body of water of claim 8, further including a plurality of algae storage tanks mounted on the deck each collecting algae from one of the process channel sections.

11. The apparatus for harvesting algae from an open body of water of claim 8, wherein the spaced apart members comprise substantially flat walls facing each other, the walls acting to contain and direct algae received between the walls for feeding to the separating mechanism.

12. The apparatus for harvesting algae from an open body of water of claim 8, wherein the process channel includes vinyl sheeting defining walls of the process channel, a plurality of piping supports, a baffle, and multiple sections of the diffused air piping.

13. The apparatus for harvesting algae from an open body of water of claim 8, further including a trash guard at an inlet of the process channel.

14. An apparatus for harvesting algae from an open body of water, comprising:
   a boat having a pair of spaced apart parallel flotation members, the flotation members defining substantially flat walls, and a deck disposed on and connected to the members, the walls defining an area therebetween forming a process channel through which water containing algae flows; and
   a separating mechanism disposed on the boat separating the process channel into a plurality of process channel sections arranged in series, the process channel sections disposed intermediate the flotation members, each of the process channel sections including a deflector plate below a water level, a scum beach crossing the water level, a scum trough coupled to the scum beach, and diffused air piping, with the diffused air piping in fluid communication with a dissolved air flotation system, wherein the walls contain and direct algae received between the walls for feeding to the separating mechanism.

15. The apparatus for harvesting algae from an open body of water of claim 14, further including mounted on the deck a saturator, a dissolved air flotation (DAF) pump, a DAF air compressor, a vacuum pump, and multiple algae storage tanks.

16. The apparatus for harvesting algae from an open body of water of claim 14, further including a trash guard positioned at a forward end of the process channel and at least partially below a water level to permit entrance of water containing algae into the process channel, while blocking large elements from entering the process channel.

17. The apparatus for harvesting algae from an open body of water of claim 14, further including a submersible fountain pump positioned within the process channel.

* * * * *